United States Patent
Pardinas et al.

[11] Patent Number: 5,299,446
[45] Date of Patent: Apr. 5, 1994

[54] METHOD AND APPARATUS FOR CALIBRATING A MULTIPLE PORT PUMP

[75] Inventors: Guillermo P. Pardinas, Miami, Fla.; Robert E. Ennesser, III, Winthrop Harbor, Ill.

[73] Assignee: Abbott Laboratories, Abbott Park, Ill.

[21] Appl. No.: 722,994

[22] Filed: Jun. 28, 1991

[51] Int. Cl.$^5$ .................................. G01F 25/00
[52] U.S. Cl. .......................................... 73/3
[58] Field of Search .......... 73/3, 1 E; 417/63, 494, 417/500, 502, 520, 461

[56] References Cited

U.S. PATENT DOCUMENTS

| | | | |
|---|---|---|---|
| 2,122,148 | 6/1938 | Lawrence | 417/461 |
| 3,994,153 | 11/1976 | Gussman et al. | 73/3 |
| 4,797,073 | 1/1989 | Kubota | 417/461 |

FOREIGN PATENT DOCUMENTS

| | | | |
|---|---|---|---|
| 89040 | 4/1937 | France | 417/461 |
| 588785 | 3/1946 | United Kingdom | 417/461 |

*Primary Examiner*—Robert Raevis
*Attorney, Agent, or Firm*—Richard D. Schmidt

[57] ABSTRACT

A method and apparatus for calibrating a multiple port metering pump includes a graduated scale mounted on the head of the pump and an indicator mounted on the body of the pump, whereby the angular orientation of a plurality of radially extending, sequentially spaced outlet ports may be adjusted relative to the pump piston to calibrate and balance the flow of fluid therethrough.

11 Claims, 2 Drawing Sheets

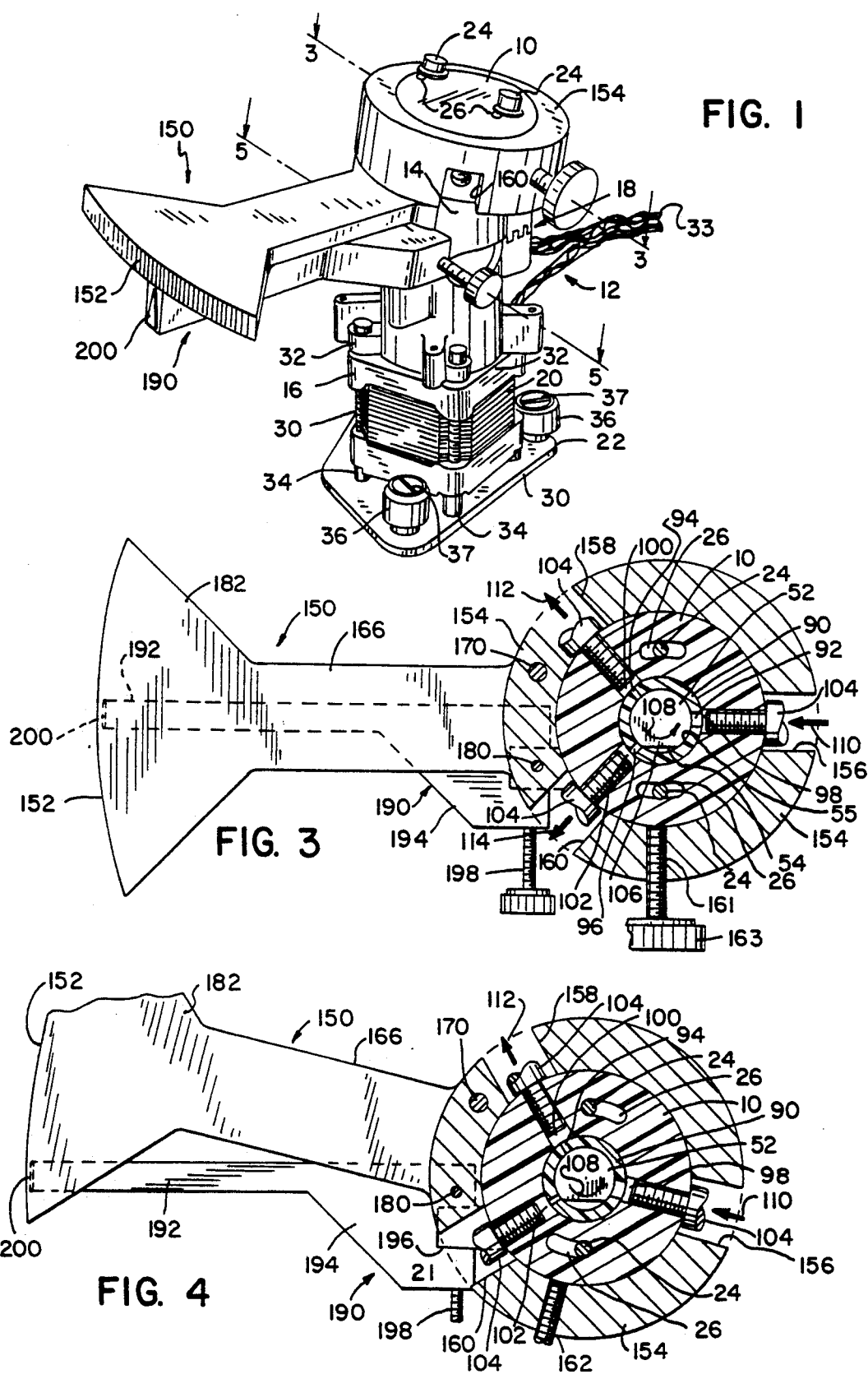

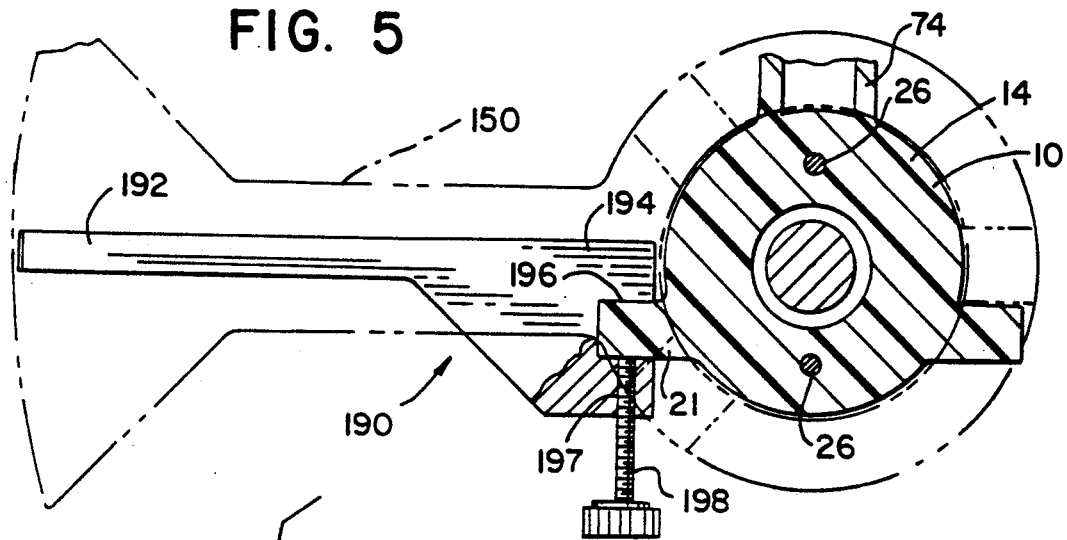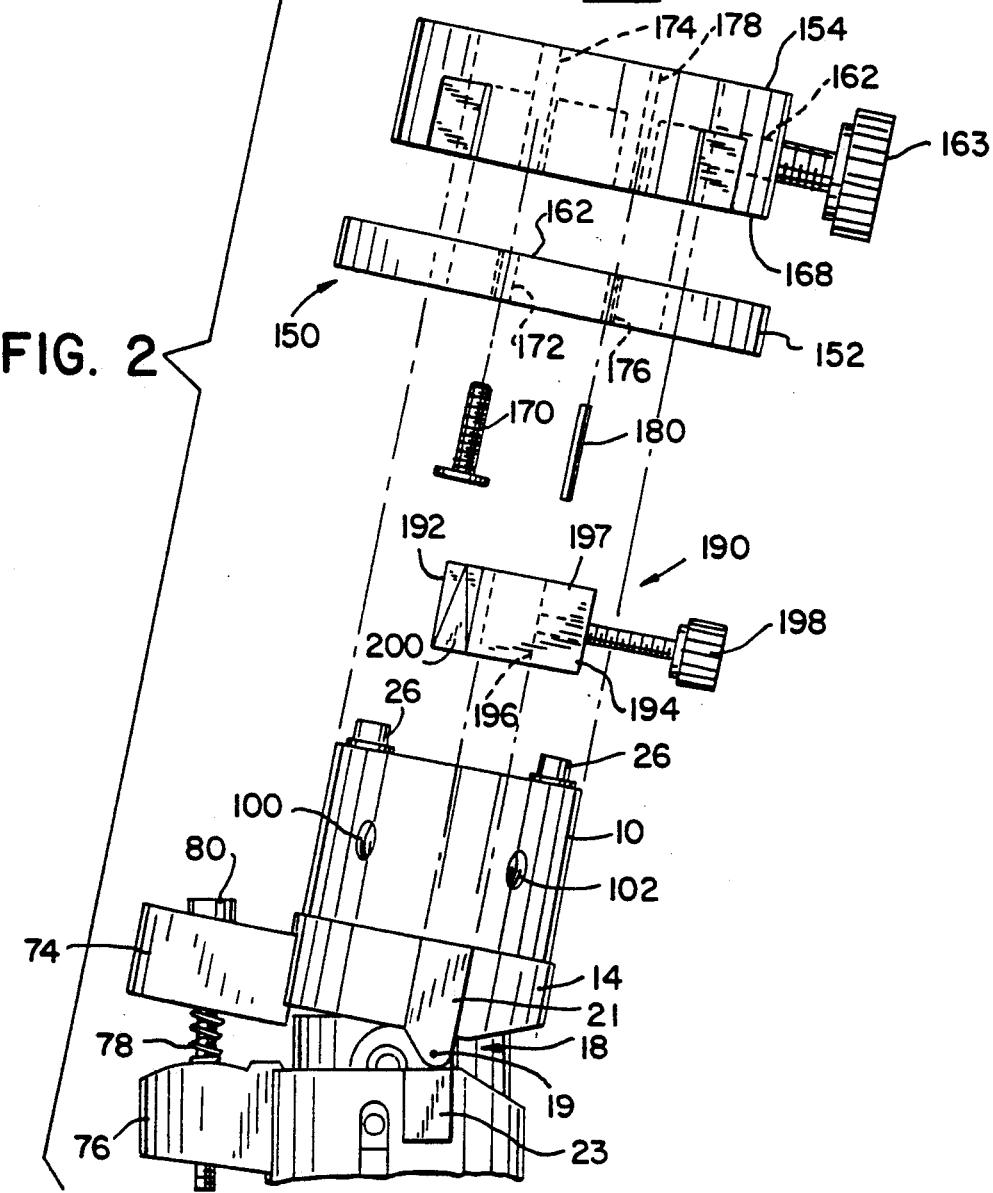

METHOD AND APPARATUS FOR CALIBRATING A MULTIPLE PORT PUMP

BACKGROUND OF THE INVENTION

1. Field of the Invention

The invention is generally related to multiple port metering pumps for delivering precise volumes of fluid and is specifically related to a method and apparatus for calibrating a multiple port pump for precisely dispensing reagents in assay tests from a plurality of outlet ports.

2. Description of the Prior Art

This invention is related to the co-pending applications entitled: VALVELESS METERING PUMP WITH RECIPROCATING ROTATING PISTON, Ser. No. 07/648,242, by G. Pardinas, filed on Jan. 31, 1991 and CONTROL SYSTEM FOR VALVELESS METERING PUMP, by R. Young et al filed concurrently herewith both of which are assigned to the assignee of this application.

It is known to use assay testing to determine the presence of infectious diseases such as, hepatitis, syphilis and the HIV virus in the presence of blood serum. In typical procedures, a precise volume of a biological sample is disposed in a test receptacle and a reagent is added to the same to perform an immunoassay using an automated analyzer. Typically, the reagent is delivered in precise volume to the testing site. The reagent volume for each sample can be in the range of 50 to 100 microliters and must be dispensed within a plus or minus 0.5 microliter accuracy and precision with less than one percent coefficient of variance.

Because of the high precision requirements of pump systems for delivering reagents, the drop size, the condition of the meniscus at the end of the outlet ports and the pressure variation due to valve movement must all be taken into consideration to assure accurate test samples. For example, the minuscule pumping action inherent in shifting a valve from one position to another is of critical significance when dealing with the volumes commonly associated with assay type testing. This, coupled with the requirement that the components of the pump which come into contact with the reagent must be of an inert material such as tetrafluro plastics and/or ceramics or the like, has led to very expensive and complex designs. Unfortunately, the more complex the design the greater the likelihood for error in manufacturing and assembly, further increasing the cost by requiring tight tolerances to minimize the effect of tolerance stacking. In addition, more complex systems with the associated number of moving parts contribute to field failure and maintenance costs.

More recently, valveless, positive displacement metering pumps have been successfully employed in applications where safe and accurate handling of fluids is required. The valveless pumping function is accomplished by the simultaneous rotation and reciprocation of a piston in a work chamber. The piston head containing the work chamber and piston is mounted such that it may be swiveled with respect to the rotating drive. The degree of angle controls the stroke and length and in turn, the flow rate. This type of pump has been found to be useful in performing accurate transfers of both gaseous and liquid fluids.

An example of a valveless positive displacement pump is disclosed in U.S. Pat. No. 4,008,003. The pump includes a cylinder divided into a pair of working chambers, each of the chambers communicating with an inlet and an outlet port. The pump disclosed in the 4,008,003 patent does not lend itself to accurate calibration for metering and dispensing fluids in the precise volumes called for in assay type tests. The piston stroke is not easily adjusted and the angular displacement of the ports cannot be readily calibrated. Another example of a valveless metering pump using a tiltable housing to control the piston stroke is disclosed in the co-pending application Ser. No. 07/463,260, entitled: PUMP WITH MULTI-PORT DISCHARGE, filed on Jan. 10, 1990, with the co-inventors G. Pardinas, R. W. Jaekel and D. Pinkerton.

A valveless metering pump specifically designed for assay type testing and for providing accurate and precise delivery of fluids to test receptacles is disclosed in my afore-mentioned related application entitled: VALVELESS METERING PUMP WITH RECIPROCATING, ROTATING PISTON, Ser. No. 07/468,262. The valveless metering pump thereshown provides a fluid delivery system particularly suited for precision delivery of fluid reagents to a test site in an assay test in a dependable and reliable manner. The pump design includes a minimum number of moving parts, is valveless, flexible in configuration and is easy to assemble with minimum risk of tolerance stacking. The pump is designed to have a broad reagent compatibility and is capable of dispensing fluid volumes in the range of 50–100 microliters per port within plus or minus 0.5 microliters and with a precision of less than one percent coefficient of variance.

It has become common practice that each pump may deliver a specific reagent to each of a plurality of testing locations and, in the prior art, a valve mechanism is used to control the flow of the reagent from first one station and then to the other. In dual port or multiple port systems, it is important that the fluid reagent delivered at each output port be balanced and accurately controlled to assure consistency in the testing procedure. This is a problem of some significance with respect to valveless metering pumps such as those disclosed in the aforementioned pending application Ser. Nos. 07/463,260; and 07/468,262.

While each of the pumps there disclosed is operative to deliver a precise and repeatable volume of fluid to the respective test receptacles, calibration of the pumps to balance the output ports can be a tedious and time-consuming task. Once the pumps are installed and in the field, re-calibration during servicing and maintenance can be difficult if not impossible, often requiring that the pump be removed and returned to the manufacturer for calibration and balancing of the output ports.

SUMMARY OF THE INVENTION

The present invention is directed to a method and apparatus for calibrating multiple port systems both during original manufacture and during service and maintenance operations after the pumps are installed in the field. Typically, the valveless metering pump includes a head having a plurality of sequential, radially spaced inlet and outlet ports in communication with a central working chamber. The pump head is adapted to be angularly adjusted about the axis of the working chamber for adjusting the relationship between each of the ports and the head of the piston to balance the fluid flow of the ports relative to one another. In the preferred embodiment of the invention, means are provided for accurately adjusting and reading the angular orientation of the pump head relative to the piston chamber. A removable calibrator having an enlarged, graduated scale is mounted on the pump head and is movable therewith. A stationary pointer is adapted to be mounted on the pump body and includes an indicator in communication with the scale for determining the precise angular position of the pump head relative to the piston for controlling and balancing the fluid flow through the radially disposed multiple ports.

The present invention readily permits calibration of the pump to accommodate for the pressure differential of the fluid as it is released from the sequential outlet ports for balancing the quantity of fluid delivered to a plurality of sequential test sites. The present invention compensates for the inaccuracies due to pressure differential of the fluid at sequential ports by adjusting the position of the ports relative to the piston as it completes its cycle.

The method and apparatus for calibrating the valveless metering pump in accordance with the subject invention provides for a fluid delivery system which is particularly well suited for precision delivery of fluid reagents to a plurality of test sites during an assay test in a dependable and reliable manner. The inlet and outlet ports of the head are in co-planar relationship and are radially spaced outwardly from the pump working chamber. The angular orientation of the ports may be readily calibrated relative to the piston to balance the pump action. The pump is designed to have a broad reagent compatibility and is capable of dispensing fluid volumes in the range of 50 to 100 microliters per port within plus or minus 0.5 microliters and with a precision of less than one percent coefficient of variance. The subject invention provides for a method and apparatus for calibrating the pump in a predictable, repeatable manner with a minimum amount of difficulty both during the manufacturing process and under field conditions.

It is, therefore, an object and feature of the subject invention to provide for a means and method for calibrating and balancing a multiple port valveless, positive displacement metering pump for accurately and precisely dispensing minute volumes of fluid through a plurality of outlets.

It is another object and feature of the invention to provide for a calibration apparatus and procedure which are readily installed on and used with the pump for calibration during service and maintenance operations.

It is an additional object and feature of the present invention to provide a means and method for calibrating and balancing a plurality of output ports in a valveless positive displacement metering pump.

Other objects and features of the invention will be readily apparent from the drawing and description of the preferred embodiment which follow.

BRIEF DESCRIPTION OF THE DRAWINGS

FIG. 1 is an assembled perspective view of the calibration system of the subject invention shown as used in conjunction with a multiple port positive displacement metering pump.

FIG. 2 is an exploded perspective view of the calibration system shown in FIG. 1.

FIG. 3 is a section view taken generally along the line 3—3 of FIG. 1.

FIG. 4 is a view similar to FIG. 3, showing the calibration system, and pump at one extreme of the calibration range.

FIG. 5 is a section view taken generally along the line 5—5 of FIG. 1.

DETAILED DESCRIPTION OF THE PREFERRED EMBODIMENT

As shown in FIG. 1 of the drawing, the valveless metering pump includes a head 10, a body 12 including an upper section 14 and a lower section 16 hingedly secured to one another at 18 (see FIG. 2). The lower body section 16 is mounted on a motor 20, which is in turn mounted on a support plate 22. The head 10 is mounted on the upper section 14 of the body via mounting screws 24 which pass through clearance slots 26 provided in the head and are received by tapped holes (not shown) in the upper body section 14. The motor 20 is mounted on the support plate 22 by suitable mounting screws 30 which pass through the clearance holes (not shown) provided in the support plate and through spacers 34 to be received by tapped holes (not shown) in mounting pads 32 of the lower body portion 16. Spring loaded mounting washers 36 are located on the support plate 22 outside the perimeter of the motor 20 and include nested mounting screws 37 for mounting the assembled pump in an operating station (not shown). The motor is connected to a power source to control and power harness 33 (see FIG. 1). As more fully described in my aforementioned co-pending application Ser. No. 07/648,242, entitled: VALVELESS METERING PUMP WITH RECIPROCATING ROTATING PISTON, incorporated by reference herein, the motor 20 typically includes an elongate cylindrical drive shaft which defines the drive axis of the pump.

The upper body section 14 of the pump body is hingedly mounted on the lower body section at 18 via hinge pins 19 (FIG. 2) As is typical, the hinge pin passes through a through hole provided in hinge pad 21 of the upper body section 14 and is received by a complementary hole in the mated hinge pad 23 of the lower body section 16. The head 52 of the piston (FIG. 3) extends into the working chamber 54 of the pump head 10. A slotted seat or extension 74 (FIG. 2) is provided in the upper body section 14 and is located radially outward and diametrically opposite the center of the hinge pin 19. A complementary slotted seat or extension 76 is provided on the lower body section 16. In the preferred embodiment, a compression spring 78 is disposed between seats 74 and 76 and a threaded adjustment screw 80 is passed through the slot in the seat 74, through the center of spring 78 and through the clearance slot in seat 76. A nut (not shown) is threadably received by the adjustment screw 80, whereby the angle of tilt between the upper body portion 14 and the head 10 relative to the lower body portion 16 and the drive axis may be adjusted by turning screw 80.

In the preferred embodiment, the pump head 10 may be made of any suitable material and includes an inert insert 90 made of ceramics or the like which includes the accurately dimensioned inner cylindrical side wall 55 of the pump working chamber 54, as best illustrated in FIGS. 3 and 4. As thereshown, the insert 90 includes three precisely metered, coplanar orifices 92, 94 and 96. The head 10 includes three corresponding cylindrical channels 98, 100 and 102. The channels 98, 100 and 102 may be tapped for receiving threaded couplings such as the couplings 104 (FIG. 3) for attaching the assembled pump to fluid control lines in the manner well known.

The fully assembled pump, as shown in FIGS. 1 and 3, may be calibrated to adjust the length of stroke of the piston by adjusting the tilt angle between the upper body section 14 and the lower body section 16 using adjustment screw 80. The tilt angle between the upper section 14 and the lower section 16 of the pump body controls the length of the reciprocating stroke of the piston head 52. When the drive motor 20 is activated to rotate the piston head, the piston rotates and reciprocates with sinusoidal motion in response to rotation of the spindle. To balance the flow through the outlet ports, the head 10 may be calibrated by adjusting the angular position of the head relative to the piston via mounting screws 24 and calibration slots 26.

It will be noted that the piston includes a flat or duct 106 in the cylindrical outer wall of the head 52. As is shown in FIGS. 3 and 4, when the piston rotates in the direction of arrow 108, the duct 106 is moved sequentially from inlet port 92 past outlet port 94 and outlet port 96 and back to inlet port 92. In operation, the piston is entering its downstroke as it comes into contact with inlet port 92, thereby expanding the working chamber 54 to draw fluid in through the channel 98 and inlet port 92, as indicated by arrow 110. As the piston continues its rotation, it begins its upstroke as it comes in contact with the first outlet port 94, contacting the working chamber 54 for forcing a portion of the fluid out through the first outlet port 94 and associated channel 100 as indicated by arrow 112. The piston continues its upstroke as it moves into contact with the second sequential outlet port 96, further contracting the working chamber 54 and forcing additional fluid out through port 96 and the associated channel 102, as indicated by arrow 114. As the piston moves past port 96, it enters the peak of its upstroke and begin the next downstroke as it moves into contact with port 92 for again drawing fluid into the working chamber of the pump.

It has been found that the fluid flow through the outlet ports 94 and 96 can be accurately balanced by adjusting the angular position of the ports relative to the stroke of the piston by rotating the head within the range permitted by the slots 26. In the preferred embodiment, the outlet ports may be adjusted to within less than a one percent coefficient of variance for reagent fluids dispensed in the range of 50-100 microliters. Further, the reagents have been consistently dispensed within a plus or minus 0.5 microliter accuracy and precision.

In the preferred embodiment of the invention, a calibrator scale assembly 150 is adapted to be mounted on the perimeter of the head 10 and includes the graduated scale 152 for accurately indicating the angular position of the head relative to the body of the pump. In the preferred embodiment, the calibration scale assembly 150 includes a mounting ring 154 which has an internal diameter adapted to snugly fit over the outside perimeter of the circular head 10 of the pump and includes a plurality of slots 156, 158 and 160 which correspond with and are larger than the orifice openings 98, 100 and 102 in the head and the couplings 104 mounted therein. A tapped hole 161 is provided in the mounting ring 154 for receiving a mounting screw 163 which may be tightened to hold the mounting ring on the head 10. The scale includes an elongate arm 166 which is adapted to be mounted on the bottom 168 (FIG. 2) of the mounting ring 154 via suitable means such as, by way of example, the threaded mounting screw 170 which passes through the clearance hole 172 in the arm 162 and is received by a tapped hole 174 in the ring. Precision drilled holes 176 and 178 are provided in the ring 154 and the arm 162, respectively, and are adapted to receive a plug fit locator pin 180 for precisely maintaining the alignment between the mounting ring 154 and the scale arm 162. The arm 162 extends radially outward from the ring and terminates in an enlarged fan-shaped scale member 182 having a graduated scale 152 on its outer surface. In the preferred embodiment, the scale 152 is located on a radial surface disposed on an arc having its center conforming substantially to the center of the mounting ring 154, when installed on the pump, and the central axis of the work chamber 54 of the pump head 10.

The calibrator indicator assembly 190 comprises an elongate arm 192 terminating at one end in a slotted mounting bracket 194 which includes a slot 196 dimensioned to be snugly received by the hinge pad 21 of the upper body portion 14 of the pump. The mounting bracket 194 includes a tapped hole 197 adapted for receiving the mounting screw 198, whereby the indicator assembly 190 may be mounted on and secured to the hinge pad 21, as shown in FIG. 5. The elongate arm 192 extends radially outward from the pump body and terminates in a pointer 200 (FIGS. 1 and 2) which is disposed in communication with the graduated scale 152 of the calibrator assembly 150.

The alignment of the outlet ports 100 and 102 of the pump relative to the piston 52 may be accurately positioned using the scale 152 in combination with the pointer 200. The calibration mechanism is functional to assist the calibration and balancing of the pump during manufacturing and assembly and to recalibrate the pump in the field during service and maintenance operations. In operation, the calibration mechanism may be readily mounted on the pump without removing the pump from service. This permits reading the pump position prior to disassembly and then reassembling the pump after service and/or maintenance. To adjust the angle of orientation of the ports relative to the piston, the mounting screws 24 in the head 10 are loosened and the pump may be angularly rotationally adjusted as shown in FIGS. 3 and 5, within the range of the slots 26 to precisely balance the pump.

While certain features and embodiments of the invention have been described herein, it will be readily understood that the invention encompasses all modifications and enhancements within the scope of the following claims.

We claim:

1. A calibrator for balancing a plurality of output ports in a metering pump of the type having a head including a plurality of radially extending, sequentially spaced ports, a body for supporting the head, a central work chamber in the head and in communication with the ports and a working piston carried in the body and in communication with the work chamber, the head and body having a common axis and the head rotatable about the axis relative to the body, the calibrator comprising:

a. a first assembly adapted to be mounted on said head outer end and extending radially outward therefrom and terminating in an outer end having an enlarged fan shaped plate terminating in an arcuate edge, the center of the arc coincidental with the cylindrical axis of said head when installed thereon, said arcuate edge further including a graduated scale corresponding to the angular position of the head relative to the body; and b. a second assembly adapted to be mounted on said body and extending radially outward therefrom and terminating in an outer end in substantial alignment with the graduated scale, whereby the angular relationship between the head and body is in direct correspondence with the angular relationship between said graduated scale and said outer end.

2. The calibrator of claim 1, wherein said head is of cylindrical cross-section and includes a cylindrical outer wall, and wherein said first assembly includes an annular ring having a diameter dimensioned to be snugly fitted over the cylindrical outer wall of the head and an arm extending radially outward from said ring and terminating in said first outer end.

3. The calibrator of claim 2, wherein the center of the arc of said fan-shaped plate is coincidental with the center of the annular ring.

4. The calibrator of claim 2, wherein said arm includes a mounting hole and an alignment hole and said ring includes a radially extending flat wall portion having a complementary mounting hole and alignment hole, further including first means passing through the respective mounting holes for securing the arm to the ring and second means passing through and forming a plug fit with the respective alignment holes for maintaining the arm in radial alignment with the ring.

5. The calibrator of claim 2, said ring including a plurality of through slots spaced radially about the periphery thereof and adapted to be positioned in alignment with the spaced ports in said head when mounted thereon.

6. The calibrator of claim 2, said ring further including a tapped through hole extending radially through said ring and a first threaded calibrator set screw adapted to be received in said tapped hole and having an end adapted for engaging the outer cylindrical wall of said head for securely holding said ring on said head.

7. The calibrator of claim 6, wherein said second assembly further includes an elongate arm having an inner end terminating in a mounting bracket and adapted to be securely mounted on said body and an opposite end defining said second outer end, the opposite end including an indicator for providing a visual reading of the position of the first outer end relative to said second outer end.

8. The calibrator of claim 7, wherein said pump body includes a protruding mounting pad and wherein said bracket includes a slot adapted for snugly engaging said protruding mounting pad for securely mounting the indicator in radial alignment with the piston of said pump.

9. The calibrator of claim 8, said bracket further including a tapped through hole disposed in communication with said protruding mounting pad when the bracket is mounted thereon and a second threaded calibrator set screw adapted to be received in said tapped hole and having an end for adapting for engaging the protruding mounting pad for securely holding said bracket on said body.

10. A method for adjusting the angular position of radially disposed ports in a pump head relative to a coaxial pump body, comprising the steps of:

a. releasably mounting a radially extending first calibrator means to the head;

b. releasably mounting a radially extending second calibrator means to the body;

c. positioning and reading the angular displacement between said first and second means for determining the corresponding position of the ports relative to the body; and d. securing the head relative to the body when a predetermined angular displacement is achieved.

11. The method of claim 10, including the additional steps of removing said first and second calibrator means after said securing step is completed.

* * * * *